(12) United States Patent
Güthner et al.

(10) Patent No.: US 7,002,038 B2
(45) Date of Patent: Feb. 21, 2006

(54) METHOD FOR PRODUCING 3-AMINO-4,4,4-TRIFLUOROCROTONIC ACID ESTERS

(75) Inventors: Thomas Güthner, Trostberg (DE); Doris Krammer, Truchtlaching (DE)

(73) Assignee: Degussa AG, Trostberg (DE)

( * ) Notice: Subject to any disclaimer, the term of this patent is extended or adjusted under 35 U.S.C. 154(b) by 10 days.

(21) Appl. No.: 10/511,932

(22) PCT Filed: Aug. 13, 2003

(86) PCT No.: PCT/EP03/09006

§ 371 (c)(1),
(2), (4) Date: Oct. 18, 2004

(87) PCT Pub. No.: WO2004/016579

PCT Pub. Date: Feb. 26, 2004

(65) Prior Publication Data

US 2005/0182272 A1    Aug. 18, 2005

(30) Foreign Application Priority Data

Aug. 14, 2002   (DE) .................... 102 37 285

(51) Int. Cl.
    *C07C 229/00* (2006.01)
(52) U.S. Cl. ..................... 560/172
(58) Field of Classification Search ............... None
    See application file for complete search history.

(56) References Cited

U.S. PATENT DOCUMENTS

| | | | |
|---|---|---|---|
| 4,647,689 A | 3/1987 | Micinski | |
| 4,883,904 A | 11/1989 | Amiet et al. | |
| 5,777,154 A | 7/1998 | Chong et al. | |
| 5,910,602 A | 6/1999 | Chong et al. | |
| 6,423,866 B1 | 7/2002 | Braun et al. | |

FOREIGN PATENT DOCUMENTS

| | | |
|---|---|---|
| EP | 0 206 953 A | 12/1986 |
| EP | 0808826 A | 11/1997 |
| WO | WO-99 24390 A | 5/1999 |
| ZA | 9704317 A | 11/1997 |

*Primary Examiner*—Paul A. Zucker
(74) *Attorney, Agent, or Firm*—Fulbright & Jaworski L.L.P.

(57) ABSTRACT

A process is described for preparing 3-amino-4,4,4-trifluorocrotonic esters of the formula (I) or the E/Z isomers or tautomeric forms thereof

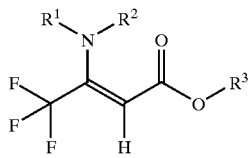
(I)

where $R^1$ and $R^2$ are each independently hydrogen, an optionally substituted linear $C_1$–$C_4$-alkyl radical or an optionally substituted benzyl radical and $R^3$ is methyl or ethyl, which comprises a) reacting an alkyl trifluoroacetate with an alkyl acetate of the formula $CH_3$—CO—$OR^3$ and an alkali metal alkoxide to give an enolate of a trifluoroacetoacetic ester of the formula (II)

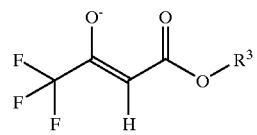

(II)

where M is sodium or potassium and $R^3$ is as defined above, and subsequently b) allowing the alkali metal enolate of the trifluoroacetoacetic ester from stage a) to react without further purification directly with an amine of the formula $NHR^1R^2$ in the presence of an acid to give the 3-amino-4,4,4-trifluorocrotonic ester.

With the aid of this two-stage process, the 3-amino-4,4,4-trifluorocrotonic esters can be prepared in high yields without significant by-products.

22 Claims, No Drawings

METHOD FOR PRODUCING 3-AMINO-4,4,4-TRIFLUOROCROTONIC ACID ESTERS

This is a §371 from PCT/EP2003/009006 filed Aug. 13, 2003 which claims priority from German 102 37 285.3 filed Aug. 14, 2002, each of which are incorporated herewith by reference in its entireties.

The present invention relates to a process or preparing 3-amino-4,4,4-trifluorocrotonic esters or the E/Z-isomers or tautomeric forms thereof.

These 3-amino-4,4,4-trifluorocrotonic esters are important intermediates or the preparation of biologically active substances, especially of crop protectants (cf. U.S. Pat. No. 6,207,830 and JP 2002-003480).

The preparation of 3-amino-4,4,4-trifluorocrotonic esters is known in principle. For example, 4,4,4-trifluoroacetoacetic esters can be reacted with amines under dehydrating conditions, optionally in the presence of an acid. In this case, a salt of the formula (III) may occur as an intermediate.

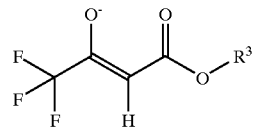

(III)

Such reactions are described, for example, in WO 99/24 390, EP-A 808 826, JP-A 06321877, JP-A 05140060 or A. N. Fomin et al., Zh. Org. Khim. 22, 1603 (1986).

All of these known process variants are based on the use or an isolated trifluoroacetoacetic ester, or example the methyl or ethyl ester. Although they are commercially available, such trifluoroacetoacetic esters have high preparation costs and a high market price owing to their very complicated purification which includes the removal or conversion of hydrates, hemiacetals and acetals (cf. U.S. Pat. No. 4,647,689 and EP-A 206 953 and literature cited therein). This circumstance leads to high preparation costs for the corresponding 3-amino-4,4,4-trifluorocrotonic esters and the end products prepared therefrom, so that the economic viability of these active ingredients is placed in doubt.

It is therefore an object of the present invention to develop an economically viable process for preparing 3-amino-4,4, 4-trifluorocrotonic esters of the general formula (I)

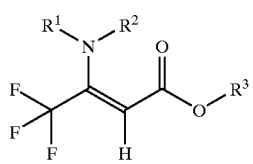

(I)

where
$R^1$ and $R^2$=H, optionally substituted linear $C_1$–$C_4$-alkyl radical or benzyl radical and
$R^3$=methyl or ethyl,
which does not have the disadvantages of the prior art mentioned, and instead can be used, starting from inexpensive raw materials and using uncomplicated apparatus, to prepare the corresponding 3-amino-4,4,4-trifluorocrotonic esters in high yields and in an inexpensive manner.

According to the invention, this object is achieved by
a) reacting an alkyl trifluoroacetate with an alkyl acetate of the formula $CH_3$—CO—$OR^3$ and an alkali metal alkoxide to give an enolate of a trifluoroacetoacetic ester of the formula (II)

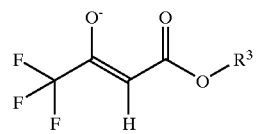

(II)

where
M=Na or K and
$R^3$ is as defined above, and subsequently
b) allowing the alkali metal enolate of the trifluoroacetoacetic ester from stage a) without further purification to react directly with an amine of the formula $NHR^1R^2$ where $R^1$ and $R^2$ are each as defined above in the presence of an acid to give the 3-amino-4,4,4-trifluorocrotonic ester.

It has been found that, surprisingly, with the aid of the inventive two-stage reaction, the 3-amino-4,4,4-trifluorocrotonic esters of the formula (I) can be prepared in high yields without significant by-products. A particularly surprising fact is that these reactions can also be carried out without losses as a "one-pot variant".

In the first stage a) of the process according to the present invention, an alkyl trifluoroacetate is reacted with an alkyl acetate in the presence of an alkali metal alkoxide in a manner known per se (cf. J. Burdon et al., Tetrahedron 20, 2163 (1964)).

In this reaction, preference is given to a molar ratio of alkyl trifluoroacetate to alkyl acetate of from 1:1 to 1:5, and excess alkyl acetate may serve as a solvent. The alkyl trifluoroacetates and alkyl acetates used are preferably the methyl esters or ethyl esters.

Reaction stage a) proceeds with addition of from 0.9 to 3 mol, preferably from 1.0 to 1.5 mol, of an alkali metal alkoxide per mole of alkyl trifluoroacetate. The alkali metal alkoxide may be used in solid form or as an alcoholic solution. Preference is given to sodium methoxide, sodium ethoxide, potassium methoxide and potassium ethoxide, and a preferred alkoxide is that of the alcohol corresponding to the esters. The reaction can proceed at a temperature of from 0 to 100° C. In reaction stage a), a suspension or solution of an alkali metal enolate of the trifluoroacetoacetic ester of the formula (II) is obtained

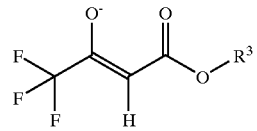

(II)

where
M=Na or K and
$R^3$ is as defined above.

It is to be regarded as essential to the invention that, after reaction stage a), the trifluoroacetoacetic ester (or its hydrate, hemiacetals or acetals) is not, as is the case in the known processes, released, isolated and purified, but rather the crude alkali metal enolate of the trifluoroacetoacetic ester is used directly for the subsequent reaction stage b). In a preferred embodiment, the reaction stages a) and b) are carried out successively in the same reaction vessel.

In this second reaction stage b) of the process according to the invention, optionally after removal of excess acetic ester and/or alcohol, the resulting alkali metal enolate of the trifluoroacetoacetic ester is reacted with an amine of the formula $NHR^1R^2$ or a salt thereof, optionally in the presence of an acid.

In the amines of the formula $NHR^1R^2$, $R^1$ and $R^2$ are each independently defined as follows: hydrogen, a linear $C_1$–$C_4$-alkyl radical or a benzyl radical. The alkyl radical or the benzyl radical may be substituted, in which case substituent groups are preferably linear or branched alkyl, alkenyl or alkynyl groups which optionally include one or more heteroatoms (O, S or N) and in each case have at most 10 carbon atoms or heteroatoms. Preferred amines are ammonia, methylamine, ethylamine, benzylamine, dimethylamine and diethylamine.

It is possible in the context of the present invention to use the amine as the free base in anhydrous form or in aqueous solution.

Instead of the free amine base, a salt thereof with an inorganic or organic acid may also be used. Preferred salts are the hydrochlorides, sulfates, nitrates, formates and acetates of the appropriate amine.

The reaction of the crude alkali metal enolate of the trifluoroacetoacetic ester with the amine of the formula $NHR^1R^2$ is preferably carried out in the presence of an excess of an acid, i.e. at a pH<7. Preferred acids are customary organic or inorganic acids, for example hydrochloric acid, anhydrous hydrogen chloride, sulfuric acid, nitric acid, formic acid or acetic acid.

The use of acetic acid and/or hydrochloric acid is to be regarded as preferred.

When a salt of an amine base is used, preference is given to using the corresponding acid in excess.

Per mole of originally used alkyl trifluoroacetate, typically from 1.0 to 10.0 mol, preferably from 1.1 to 4.0 mol, of amine of the formula $NHR^1R^2$ (or a salt thereof) are used. The molar amount of the acid to be used depends upon the originally used amount of the alkali metal alkoxide and the amount of amine used, and is typically from 1.0 to 10.0 mol, preferably from 1.1 to 4.0 mol, per mole of alkyl trifluoroacetate used. Any amount of acid present in the amine salt used has to be taken into account here. Preference is given to using a molar amount of acid which is greater than the number which is calculated from the moles of alkali metal alkoxide used plus the moles of amine used minus the moles of alkyl trifluoroacetate originally used.

The reaction of the crude alkali metal enolate of the trifluoroacetoacetic ester with the amine in the presence of the acid is effected typically at temperatures of from 20 to 200° C., in particular from 50 to 160° C. Preference is given to carrying out the reaction with continuous removal of the water of reaction formed. This can be effected, for example, by distilling off the water of reaction at the reaction temperature, optionally under reduced pressure. In a particular embodiment, the removal of the water of reaction is eased by an inert azeotroping agent. Preferred azeotroping agents are hydrocarbons in the boiling range between 50 and 150° C., for example hexane, octane, cyclohexane, methylcyclohexane, benzene, toluene and xylenes.

The resulting reaction mixture is, optionally after an extraction, freed of by-products (alkali metal salts, amine salts and acids) by filtration and/or washing, and subsequently subjected to a fractional distillation, optionally a multistage fractional distillation, under atmospheric pressure or reduced pressure.

The desired 3-amino-4,4,4-trifluorocrotonic ester is obtained as the distillate in good yield and high purity.

The examples which follow are intended to illustrate the process according to the invention.

EXAMPLES

Example 1

A reaction flask inertized with nitrogen was initially charged with 142.1 g (1.0 mol) of ethyl trifluoroacetoacetate and 176.2 g (2.0 mol) of ethyl acetate. With intense cooling, 68.1 g (1.0 mol) of solid sodium ethoxide were added at from 18 to 20° C. within 30 minutes. The mixture was then stirred at 30° C. for 30 minutes and at 76° C. for a further 4 hours.

Excess ethyl acetate and ethanol formed were distilled off at approx. 600 mbar. The resulting brown, slurry-like crude sodium enolate of ethyl trifluoroacetoacetate was suspended in 500 ml of cyclohexane.

78.0 g (1.3 mol) of anhydrous acetic acid were added to this mixture. Within 1 hour, 100.9 g (1.3 mol) of 40% aqueous methylamine solution were metered in, in the course of which the temperature rose from approx. 30 to 50° C.

The suspension was heated to boiling, the water was removed from the distillate which separated, and the cyclohexane was returned back into the reaction mixture. After 5 hours, no further water separated out; the reaction was terminated.

At 20° C., 800 ml of water were added to the suspension, and a liquid biphasic system formed. The aqueous phase was removed; the organic phase was washed once more with 100 ml of water and dried over sodium sulfate.

The cyclohexane was distilled off and the product was then fractionated at 350 mbar/approx. 98° C. 143 g of ethyl 3-methylamino-4,4,4-trifluorocrotonate were obtained. The yield was 73%, the gas chromatography purity was >99%.

EI mass spectrum: $M^+$=197 amu, fragments 168, 152, 150, 138, 125, 110, 82 amu. $^1H$ NMR: 8.2 ppm (NH), 4.95 ppm 1H (CH), 4.11 ppm quartet 2H (ethyl), 2.92 ppm doublet*quartet 3H (NCH$_3$), 1.3 ppm triplet 3H (ethyl), $^{13}C$ NMR: 168 ppm (COOEt), 148 ppm quartet (C—NHMe), 120 ppm quartet (CF$_3$), 82 ppm quartet (CH), 59 ppm (ethyl), 30 ppm quartet (CH$_3$N), 13 ppm (ethyl).

Example 2

142.1 g (1.0 mol) of ethyl trifluoroacetoacetate and 176.2 g (2.0 mol) of ethyl acetate were reacted in a similar manner to example 1 with 68.1 g (1.0 mol) of solid sodium ethoxide.

After 500 ml of cyclohexane had been added, 138 g (2.3 mol) of anhydrous acetic acid and 100.9 g (1.3 mol) of 40% aqueous methylamine solution were added.

The suspension was heated to boiling, the water was removed from the distillate which separated, and the cyclohexane was returned back into the reaction mixture. After 4 hours, no further water separated out; the reaction was terminated.

At 20° C., the resulting suspension was filtered and washed twice with 100 ml each time of cyclohexane, and the cyclohexane was distilled off. The resulting crude product was fractionated at 430 mbar and approx. 120° C. through a column having random packing. 140.4 g of pure ethyl 3-methylamino-4,4,4-trifluorocrotonate having a content of 98.8% were obtained. The yield was 71%.

Example 3

71.05 g (0.50 mol) of ethyl trifluoroacetate and 88.1 g (1.0 mol) of ethyl acetate were reacted in a similar manner to example 1 with 34.05 g (0.5 mol) of solid sodium ethoxide and concentrated by evaporation to give a slurry of the sodium enolate.

After 250 ml of cyclohexane had been added, 77.1 g (1.0 mol) of ammonium acetate and 39.0 g (0.65 mol) of anhydrous acetic acid were added.

The suspension was heated to boiling, the water was removed from the distillate which separated, and the cyclohexane was returned back into the reaction mixture. After 5 hours, the reaction was terminated.

300 ml of water were added and the organic phase was removed. From the organic phase, the cyclohexane was distilled off and the product was fractionated under reduced pressure. 57.0 g of ethyl 3-amino-4,4,4-trifluorocrotonate having a content of 97.4% were obtained. The yield was 62%.

EI mass spectrum: $M^+$=183 amu. $^1H$ NMR: 7.6 ppm (NH), 4.86 ppm 1H (CH), 4.08 ppm quartet 2H (ethyl), 1.18 ppm triplet 3H (ethyl). $^{13}C$ NMR: 168 ppm (COOEt), 147 ppm quartet (C—$NH_2$), 120 ppm broad quartet ($CF_3$), 82 ppm quartet (CH), 59 ppm (ethyl), 14 ppm (ethyl).

What is claimed is:

1. A process for preparing 3-amino-4,4,4-trifluorocrotonic esters of formula (I)

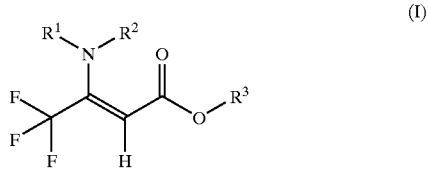

(I)

or the E/Z-isomers or tautomeric forms thereof wherein
$R^1$ and $R^2$ are each independently hydrogen, an optionally substituted linear $C_1$–$C_4$-alkyl radical or an optionally substituted benzyl radical
and
$R^3$ is methyl or ethyl, comprising
a) reacting an alkyl trifluoroacetate with an alkyl acetate of the formula $CH_3$—CO—$OR^3$ and an alkali metal alkoxide to give an enolate of a trifluoroacetoacetic ester of formula (II)

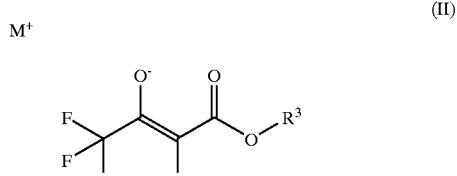

(II)

wherein
M=Na or K and
$R^3$ is as defined above,
and subsequently
b) reacting the alkali metal enolate of the trifluoroacetoacetic ester from stage a) without further purification directly with an amine of the formula $NHR^1R^2$, where $R^1$ and $R^2$ are each as defined above, in the presence of an acid to provide the 3-amino-4,4,4-trifluorocrotonic ester.

2. The process of claim 1, wherein said alkyl trifluoroacetates and alkyl acetates are the corresponding methyl or ethyl esters.

3. The process of claim 1, wherein in stage a), the molar ratio of alkyl trifluoroacetate to alkyl acetate is set to from 1:1 to 1:5.

4. The process according to claim 1, wherein from 0.9 to 3.0 mol of the alkali metal alkoxide are present per mole of alkyl trifluoroacetate.

5. The process of claim 1, wherein the alkali metal alkoxide is selected from the group consisting of sodium methoxide, sodium ethoxide, potassium methoxide and potassium ethoxide.

6. The process of claim 1, wherein the reaction in stage a) is carried out at a temperature of from 0 to 100° C.

7. The process of claim 1, further comprising removing excess alkyl acetate and/or alcohol upon completion of stage a).

8. The process of claim 1, wherein the amine $NHR^1R^2$ in stage b) is a free base in anhydrous form.

9. The process of claim 1, wherein the amine $NHR^1R^2$ in stage b) is an aqueous solution.

10. The process of claim 1, wherein the amine $NHR^1R^2$ in stage b) is in the form of a salt selected from the group consisting of hydrochloride, sulfate, nitrate, formate and acetate.

11. The process of claim 1, wherein the amine $NHR^1R^2$ is selected from the group consisting of ammonia, methylamine, ethylamine, benzylamine, dimethylamine and diethylamine, or a salt of these amines.

12. The process of claim 1, wherein from 1.0 to 10.0 mol of amine is provided per mole of alkyl trifluoroacetate.

13. The process of claim 1, wherein the acid in stage b) is present in an amount of from 1.0 to 10.0 mol per mole of alkyl trifluoroacetate.

14. The process of claim 1, wherein the acid is acetic acid and/or hydrochloric acid.

15. The process of claim 1, wherein reaction stage b) is carried out at temperatures of from 20 to 200° C.

16. The process of claim 1, wherein water of reaction is removed continuously during the reaction of stage b).

17. The process of claim 1, wherein the reaction of stage b) is carried out in the presence of an organic hydrocarbon as an azeotroping agent.

18. The process of claim 1, wherein the azeotroping agent is a solvent selected from the group consisting of hexane, octane, cyclohexane, methylcyclohexane, benzene, toluene and a xylene.

19. The process of claim 1, wherein the reaction mixture is worked up by extraction and subsequent distillation.

20. The process of claim 1, wherein stages a) and b) are carried out successively in the same reaction vessel.

21. The process of claim 1, wherein from 1.1 to 4.0 mol of amine is provided per mole of alkyl trifluoroacetate.

22. The process of claim 1, wherein reaction stage b) is carried out at temperatures of from 50 to 160° C.

* * * * *